(12) United States Patent
Underwood et al.

(10) Patent No.: US 11,104,768 B2
(45) Date of Patent: Aug. 31, 2021

(54) PROCESS FOR THE PROCESSING OF A PERFLUOROPOLYMER MATERIAL

(71) Applicant: ESP Technology Limited, Ince (GB)

(72) Inventors: Christopher John Underwood, Ince (GB); Robert Stevens, Ince (GB)

(73) Assignee: ESP TECHNOLOGY LIMITED, Ince (GB)

( * ) Notice: Subject to any disclaimer, the term of this patent is extended or adjusted under 35 U.S.C. 154(b) by 105 days.

(21) Appl. No.: 15/036,108

(22) PCT Filed: Nov. 19, 2014

(86) PCT No.: PCT/GB2014/053428
§ 371 (c)(1),
(2) Date: May 12, 2016

(87) PCT Pub. No.: WO2015/075450
PCT Pub. Date: May 28, 2015

(65) Prior Publication Data
US 2016/0289399 A1    Oct. 6, 2016

(30) Foreign Application Priority Data
Nov. 25, 2013  (GB) .................... 1320756

(51) Int. Cl.
| | | |
|---|---|---|
| B05D 3/00 | (2006.01) | |
| C08J 3/24 | (2006.01) | |
| A61L 27/34 | (2006.01) | |
| C08J 9/26 | (2006.01) | |
| A61L 27/16 | (2006.01) | |
| B05D 1/36 | (2006.01) | |
| A61L 27/56 | (2006.01) | |
| A61L 31/04 | (2006.01) | |
| A61L 31/14 | (2006.01) | |
| C08J 9/28 | (2006.01) | |
| H01M 8/0239 | (2016.01) | |

(52) U.S. Cl.
CPC ............ *C08J 3/24* (2013.01); *A61L 27/16* (2013.01); *A61L 27/34* (2013.01); *A61L 27/56* (2013.01); *A61L 31/048* (2013.01); *A61L 31/146* (2013.01); *B05D 1/36* (2013.01); *B05D 3/007* (2013.01); *C08J 9/26* (2013.01); *C08J 9/283* (2013.01); *H01M 8/0239* (2013.01); *A61L 2400/08* (2013.01); *A61L 2420/02* (2013.01); *B05D 2401/10* (2013.01); *B05D 2506/10* (2013.01); *C08J 2201/026* (2013.01); *C08J 2201/04* (2013.01); *C08J 2201/042* (2013.01); *C08J 2201/044* (2013.01); *C08J 2201/046* (2013.01); *C08J 2205/05* (2013.01); *C08J 2327/12* (2013.01)

(58) Field of Classification Search
CPC ....... C08J 3/24; C08J 9/26; C08J 9/283; C08J 2201/026; C08J 2201/04; C08J 2201/042; C08J 2201/044; C08J 2201/046; C08J 2205/05; C08J 2327/12; A61L 27/16; A61L 27/34; A61L 27/56; A61L 31/048; A61L 31/146; A61L 2400/08; A61L 2420/02; B05D 3/007; H01M 8/0239
See application file for complete search history.

(56) References Cited

U.S. PATENT DOCUMENTS

| 5,694,701 A | * | 12/1997 | Huelsman ................ F26B 3/20 |
| | | | 34/421 |
| 2003/0176516 A1 | | 9/2003 | Underwood et al. |
| 2014/0132111 A1 | | 5/2014 | Nakayama |

FOREIGN PATENT DOCUMENTS

| WO | 03078516 A1 | 9/2003 |
| WO | 2008094758 A1 | 8/2008 |

OTHER PUBLICATIONS

International Search Report corresponding to Int'l Pat. Appl. No. PCT/GB2014/053428, dated Mar. 26, 2016, 2 pages.

* cited by examiner

*Primary Examiner* — Robert S Walters, Jr.
(74) *Attorney, Agent, or Firm* — Tarolli, Sundheim, Covell & Tummino LLP

(57) ABSTRACT

The present disclosure relates to a process for the processing of perfluoropolymer materials, and to the use of the resultant products in different potential applications, such as in the medical device field. The process can include, for example, the steps of: (i) dissolving one or more uncured perfluoropolymer materials in a solvent containing one or more liquid perfluorinated solvent(s) to form a solution; (ii) optionally adding one or more porogens and/or one or more functional additives to the solution formed in (i) to form a mixture; (iii) applying the resultant solution or mixture formed in steps (i) and (ii) to a substrate to form one or more partial or continuous deposited layers on the substrate; (iv) curing the perfluoropolymer within the deposited layer to form a perfluoroelastomeric product; and (v) optionally removing the porogen from the perfluoroelastomeric product.

17 Claims, No Drawings

PROCESS FOR THE PROCESSING OF A PERFLUOROPOLYMER MATERIAL

RELATED APPLICATIONS

The present application is a U.S. National Stage application under 35 USC 371, claiming priority to Serial No. PCT/GB2014/053428, filed Nov. 19, 2014, which claims priority from GB 1320756.8, filed Nov. 25, 2013, both of which are incorporated herein by reference in their entirety for all purposes.

TECHNICAL FIELD

The present invention relates to a process for the processing of perfluoropolymer materials, and to the use of the resultant products in different potential applications, such as in the medical device field.

BACKGROUND

Perfluoropolymer, or perfluoroelastomeric, materials are well-known in the art, and are known to have high levels of chemical resistance (fluid resistance, base-resistance, dielectric properties and high temperature resistance), plasma resistance, compression set resistance (compression set is the propensity of an elastomeric material to remain distorted and not return to its original shape after a deforming compressive load has been removed; the compression set value is expressed as a percentage of the original deflection that the material fails to recover), and effective mechanical properties. As a result of these properties, they have many potential and actual applications. For example, perfluoroelastomeric materials can be used as elastomeric seals in applications where the seal or gasket will be subject to corrosive chemicals or extreme operating conditions, for use as molded parts which are capable of withstanding deformation, as well as in the semiconductor industry due to their plasma resistance. The major market (80%) is essentially solvent resistant applications. Applications of these compositions in the aerospace industry range from oxidizer resistant components to both commercial and military jet engine seals operating in a sustained high temperature environment.

FFKM gums are the precursors to elastomers, correctly defined as perfluoroelastomers (i.e. they are completely fluorinated, and contain no hydrogen atoms).

At between 71 and 72 percent, highly fluorinated FFKM elastomers have a fluorination level that is almost identical to that of pure polytetrafluoroethylene (PTFE), which has a theoretical fluorination level of 76%. This compares with 62-68% for non-wholly fluorinated fluoroelastomers. This means that, for example, Freudenberg's perfluoroelastomer Simriz® is unusually resistant to reaction media, solvents, acids, and alkali over a broad temperature and pressure range. The chemical resistance of Simriz® is so universal that it is capable of statically sealing almost every possible medium.

Other perfluoro compositions known in the art include those marketed under the trade name Fluorinert®, which are are electrically insulating, stable fluorocarbon-based fluids, and are consequently used primarily as coolant liquids for electronics. Different molecular formulations are available with a variety of different boiling points, which allows them to be used either in "single phase" applications where the composition remains in its liquid form, or in "two-phase" applications where the liquid boils to remove additional heat via evaporative cooling. An example of one of these Fluorinert® goes by the name FC-72, or perfluorohexane ($C_6F_{14}$). Perfluorohexane is used for low temperature heat transfer applications due to its boiling point of 56° C. Another example is FC-75, perfluoro(2-butyl-tetrahydrofurane). There are also fluids marketed under the Fluorinert® brand that can withstand temperatures of up to about 215° C., such as FC-70, as well as fluids marketed under the FLUTEC® brand name.

However, perfluoroelastomeric materials are expensive. As a result, the costs of materials and parts, such as seals and gaskets, are significantly greater than those found with other elastomeric materials.

As such, while the properties of perfluoroelastomers are highly desirable, their uses tend to be limited, so it would also be desirable to develop an improved method for the processing of perfluoroelastomeric materials to make final perfluoroelastomeric products for an end use.

A previous method for the processing of perfluoroelastomeric materials is described in WO 03/078516 to Greene, Tweed of Delaware, Inc and CuMedica Group PLC. This method involves combining a perfluoroelastomeric material with two perfluorosolvents, one having a high boiling point and another with a low boiling point. The boiling point of the latter solvent is sufficiently low that the solvent could be evaporated away without the need for any heat or energy being applied, aided by manual manipulation, i.e. by increasing the surface area by using a putty knife or a similar tool. Ceramic or metallic balls are added to aid mixing, and the resultant mixture is poured onto a tray or other flat surface (which could be metallic or plastic), where the low boiling point solvent is removed, and the high boiling point solvent is deliberately left behind as part of the mixture. Once the low boiling point solvent is removed, the mixture forms a solid, dough-like material on the tray. It is then manually cut up into pieces and applied to a mandrel within a compression mould, where the material is finally cured. The method in WO 03/078516 exclusively intends the perfluoroelastomeric material to be shaped in a mould via compression moulding techniques.

SUMMARY

Therefore, in accordance with the present invention, there is provided a process for the processing of a perfluoropolymer material, the process comprising the steps of:

i) Dissolving one or more uncured perfluoropolymer materials in a solvent containing one or more liquid perfluorinated solvents(s) to form a solution;

ii) If required, adding one or more porogens and/or one or more functional additives to the solution formed in (i) to form a mixture;

iii) Applying the resultant solution or mixture formed in steps (i) and (ii) to a substrate to form one or more partial or continuous deposited layers on the substrate;

iv) Applying an amount of energy to the substrate or the one or more deposited layers to at least partially remove the solvent from the one or more deposited layers; and v) Curing the perfluoropolymer material within the deposited layer to form a perfluoroelastomeric product; and vi) If desired, removing the porogen from the perfluoroelastomeric product.

DETAILED DESCRIPTION

In contrast to the method detailed in WO 03/078516, the present invention cures the perfluoropolymer material on the same substrate it is originally deposited on in step (iii), and also requires energy to remove the solvent. Advantages of the present invention include the ease of manipulation of the perfluoropolymer material and that only one single substrate is required, upon which the perfluoroelastomeric material is deposited, shaped and cured, in contrast to the metal tray and mandrel that are required in WO 03/078516; the ability to easily deposit multiple layers on the substrate, in contrast to the single layer that is permitted in WO 03/078516; and that the present method can be carried out using only one solvent in contrast to the requirement for two in WO 03/078516. Further, the present invention permits the use of directional heating, plus a permanent attachment or lamination to an ePTFE, or other suitable non-temporary (i.e. shaping or forming) substrate.

The perfluoroelastomeric products prepared according to the present invention may have a number of different uses and applications, such as for use in human and animal bodies for medical purposes, such as for implants, grafts, insertable medical devices, cardiovascular prostheses, grafts, tissue engineered products utilizing synthetic lattices (which act as a scaffold for the growth of human or animal cells within the scaffold), and other components. They also have application in internal cores and outer sheaths for sealing members, such as O-rings, gaskets, or the like.

Typical prior art elastomers or plastics used in such medical applications include polyurethanes, PTFE, expanded PTFE and silicones among others. The drawbacks of such prior art materials include, for example, that silicones, while having many acceptable properties generally do not demonstrate sufficient strength and related mechanical properties in the body, for example, exhibit poor tear strength and suture pull-out resistance.

Polyurethanes, while having excellent physical properties for some applications, can exhibit degradation, typically hydrolytic degradation, that can lead to catastrophic failure of critical medical devices. Expanded PTFE, while conformable and having excellent biocompatibility, is not sufficiently distensible and has cloth-like properties which, while acceptable for some applications such as hernia repair or a pericardial patch, are not ideal for many other applications requiring distensibility and elastomeric properties, for example, for use in blood vessels.

As used herein, a "perfluoroelastomer" may be any cured elastomeric material, derived by curing a perfluoroelastomeric material as defined herein, which includes a curable perfluoropolymer having a crosslinking group to permit curing to take place. A perfluoroelastomer is substantially completely fluorinated, and preferably completely fluorinated with respect to the carbon atoms on the backbone of the perfluoropolymer. It will be understood, based on this disclosure, that some residual hydrogen may be present in perfluoroelastomers within the crosslinks due to use of hydrogen in the functional crosslinking group in some perfluoroelastomeric materials. Perfluoroelastomers are generally cross-linked polymeric structures. The perfluoropolymers used in perfluoroelastomeric materials to form perfluoroelastomers upon cure, are formed by polymerizing one or more perfluorinated monomers, one of which is preferably a perfluorinated curesite monomer having a functional group to permit curing. One or more perfluoropolymers, and preferably at least one curing agent, are combined in a perfluoroelastomeric material which is then cured forming the resulting crosslinked elastomer, or perfluoroelastomer.

As used herein, a "perfluoroelastomeric material" or a "perfluoropolymer material" is a polymeric material including a curable perfluoropolymer formed by polymerizing two or more perfluorinated monomers, including at least one perfluorinated monomer which has at least one functional group to permit curing. Such materials are also referred to generally as FFKMs in accordance with the American Standardized Testing Methods (ASTM) definition and as described further herein.

Examples of perfluoropolymer materials that may be used according to the present invention include, but are not limited to, one or more of various perfluorinated copolymers of at least one fluorine-containing ethylenically unsaturated monomer, such as tetrafluoroethylene (TFE), hexafluoropropylene (HFP), and perfluoroalkylvinyl ethers (PAVEs) which include alkyl groups that are straight, branched and include ether linkages, such as perfluoro (methyl vinyl ether), perfluoro (ethyl vinyl ether), perfluoro (propyl vinyl ether), perfluoroalkoxyvinyl ethers and other similar compounds.

Typically, the perfluoropolymers used are terpolymers of TFE, PAVE, and at least one perfluorinated curesite monomer which incorporates a functional group to permit cross-linking of the terpolymer. Suitable curesite monomers include those having cyano curesites, bromo, iodo or pentafluorophenoxy functional groups, among others. Such monomers are well known in the art. Curing agents for use with various perfluoroelastomer compositions include bisphenols and their derivatives, tetraphenyl tin and peroxide-based curing systems. In addition, the perfluoropolymers may be cured using radiation curing technology. Such materials are all well known in the art.

Many such cured perfluoropolymers are commercially available. Preferred perfluoropolymers are used in Chemraz® parts, which are commercially available from Greene, Tweed & Co., Inc. of Kulpsville, Pa. Other preferred perfluoropolymers include perfluoroelastomeric cured Kalrez® parts and materials, which are commercially available from E. I. du Pont de Nemours of Wilmington, Del. Uncured commercial perfluoropolymers are also known, including Simriz®, which is available from Freudenberg of Germany; Dyneon®, available from Minnesota Mining & Manufacturing in Minnesota, Daiel-Perfluor®, which is available from Daikin Industries, Ltd. of Osaka, Japan. Similar materials are available also from Ausimont S. p. A. in Italy.

The preferred solvent for use in the present invention is one in which only the uncured perfluoropolymer material and/or curing agent will dissolve. Most preferably only the uncured perfluoropolymer within the perfluoroelastomeric material will dissolve without dissolving the porogen, fillers, curing agent(s) and any other additives. The preferred solvents include specialty solvents which may be used alone or in combination, and which are specifically designed for the dissolution of perfluoropolymers, including liquids which are themselves perfluorinated materials such as liquid perfluorinated compounds. Such solvents are known in the electronic industry. Suitable commercial perfluorinated solvents are available from 3M, St. Paul, Minn. as Fluorinert®, as well as under the FLUTEC® brand name from F2 Chemicals in Preston, UK.

Preferred Fluorinert® formulations include, for example, those marketed under the brand names FC-87, FC-84, FC-75 and FC-43. However, it should be understood that while such perfluorinated solvents are preferred, any known solvent, or solvent to be developed, which is capable of dissolving the perfluoropolymer within the perfluoroelastomeric material, but not the porogen, fillers, curing agent(s) and any other additives, may be used within the scope of the invention.

While more than one solvent may be used in the present invention, typically only one solvent is required.

Typically, the total amount of uncured perfluoropolymer material in the solution is up to about 30% by weight of the perfluorinated solvent(s), more typically, between about 2 to about 15%. The curing agent or agents make up a total of about 1 part to about 10 parts by weight per 100 parts by weight of the perfluoropolymer material, and more preferably about 1 to about 5 parts by weight.

Once the perfluoropolymer material and curing agent is in solution, the optional porogen(s) and any additional additives are combined in any order into the solution and dispersed to form the mixture. The porogens and additional additives which can be incorporated with the solution to form the mixture, are noted below. Such additives are preferably present in an amount of about 10 parts to about 500 parts by weight, preferably about 150 to 250 parts by weight per 100 parts by weight of the perfluoropolymer in the perfluoroelastomeric material.

Dissolution and/or combination of the components in the solution may be accomplished by any suitable mixing or blending technique. It is preferred that the solution is either not heated, or if heated, heated at a temperature below the curing temperature in order to avoid premature curing of the elastomer prior to thorough dispersion of the porogen(s) and additional additives.

Typically, a mechanical stirring system, which moves undissolved perfluoropolymer gum solids through perfluorosolvents is used to establish the solution by substantially or completely dissolving the perfluoropolymer with the perfluoro-solvent in the perfluoroelastomeric material, and in order to thoroughly and uniformly disperse the porogen, either a magnetic stirrer, multi-axis mixer, roller table or a ball mill may be used. A ball mill, homogenizer or similar apparatus can avoid agglomeration of the porogen or other particulate additives within the combined solution. Such blending or mixing should be carried out until a sufficiently combined solution of perfluoropolymer material is achieved having thoroughly dispersed curing agent and porogen, and well dispersed additives, if any.

The compositions of the invention may typically contain one or more porogens, i.e. materials that create pores within the perfluoropolymer, or act to increase its porosity. Exemplary compounds which can act as porogens within the present invention include, but are not limited to, one or more compounds selected from sodium chloride, salicylic acid, lactose, valine, sodium bicarbonate, sodium hydrogen carbonate, calcium carbonate, glycine, polyethylene oxide, polyethylene glycol (PEG), polyvinylpyrrolidone, particulate polymers (e.g. polyvinyl chloride), and/or titanium dioxide.

Typically, the porogen provides a relatively narrow particle size distribution in order to provide uniformity to the size of the open cells formed in the cured material. If such materials are not classified in this manner initially, they may be micronized or otherwise ground using a ball mill and sieve or similar apparatus to achieve such a distribution. However, if such uniformity is not desired, it will be understood that such particle size uniformity of the pore forming material is also not necessary. In a preferred embodiment according to the invention, an open-cell cellular perfluoropolymer is formed having an average pore size of from about 1 to about 150 microns. For use in certain applications, such pore forming agent should be available in a fine average particle size of greater than 0 and less than about 10 microns, a mid-range size of about 10 to about 50 microns in size and a larger size of greater than 50 microns. The mid-range size is a preferred range for use, for example, in cardiovascular prostheses.

The porogen should typically be provided in an amount of about 10 parts to about 500 parts by weight, and more typically about 50 parts to about 300 parts by weight based on 100 parts by weight of the perfluoropolymer in the perfluoropolymer material. High loadings of porogen are preferred for forming a highly porous matrix, for example, loadings of 50 parts up to 500 parts or more porogen per 100 parts of the perfluoropolymer(s) in the perfluoropolymer material can provide a porosity level (density reduction) of about 85% or more. Higher levels of porosity (and lower density), if desired, may be achieved by higher loadings. Density, particle size and quantity of porogen can all contribute to the ultimate characteristics of the cellular materials, for example, the density of the porogen can affect porosity with respect to variations in the volume of space taken up for a given amount of porogen. The higher the density of the material, the less the volume of pores for the same weight of porogen. Further, the particle size of the porogen can be varied to modify pore size and/or pore surface area.

In a further subsequent step, the porogen may be removed from the cured material, if desired.

As used herein, with respect to medical applications, a "device" is intended to have its broadest meaning including, without limitation, all types of medical devices, parts, components, vascular protheses, grafts, implants, tissue engineered products such as those using synthetic lattices for use in forming a scaffold, synthetic spinal disks, breast prostheses and any other device which can act to replace soft tissue, tubes, catheters, stents, drainage tubes, synthetic dura mater, pericardial patches, cannulae, fistulas, ports, and the like. One or more curing agents may also be added as part of the process of the invention, if desired.

According to the invention, the step (v) of the process of curing the perfluoropolymer may either be carried out when the perfluoropolymer is still on the substrate, or alternatively when the perfluoropolymer is not on the substrate. Prior to the curing step, the perfluoropolymer may be removed from the substrate and cured separately.

As noted above, the perfluoropolymer material may also include other functional materials suitable for addition to perfluoroelastomeric compounds. These include, but are not limited to, one or more fillers, such as graphite, carbon black, carbon nanotubes, clay, silicon dioxide, polymeric graphite, fluoropolymeric particulates (e.g. TFE homopolymer and copolymer micropowders), barium sulfate, silica, titanium dioxide, silver chloride, magnetite, a material (such as haematite) which can provide electrical and/or magnetic permeability and which can be inductively heated, and/or hydroxyapatite. The filler may be in any form that is suitable to the desired application of the perfluoropolymer, but it is typically in a particulate form.

By the term 'functional additive' is meant herein a material that is added to the process to perform a specific function. Examples of such additives that may be added include but are not limited to, co-agents, processing aids, including acid acceptors, cure accelerators, glass fibers, or polyaramid fibers such as Kevlar®, curatives and/or plasticizers or other additives known or to be developed in the perfluoroelastomeric art. An example of a plasticizer useful in the present perfluoropolymer material is a perfluorinated alkyl ether, such as Krytox®, which is commercially available from du Pont, Demnum®, a perfluoropolyether oil which is commercially available from Daikin and Fomblin®, another perfluoropolyether oil which is commercially available from Ausimont in Italy, with the most preferred being Demnum® S-100.

Typically, any additives are present in the composition in an amount of no greater than about 25% by weight based on the weight of the perfluoropolymer in the perfluoropolymer material.

The substrate used in the process of the invention may be of any suitable material, it may be either porous or non-porous, or it may be permanent or sacrificial. For example, the substrate may be a metallic mandrel, a non-metallic mandrel, a metallic implant, or a non-metallic implant. Suitable materials for the substrate include, but are not limited to, steel, stainless steel, glass, PTFE, or ePTFE. Whether or not the substrate is porous depends upon the application the product is to be used for.

There are a number of methods that can be used in step (iii) to apply the resultant mixture from steps (i) and (ii) to a substrate to form one or more deposited layers. These methods include, but are not limited to:

Pneumatic spraying
Electrostatically focused pneumatic spraying
Electrospraying
Ultrasonic spraying
Syringing
Electrostatic spinning
Inkjet printing
Dip coating
Brushed/painted
Any other processing method that can be used to apply a solution or liquid mixture.

Typically, the method used to apply the mixture to the substrate is a spraying technique, most typically pneumatic spraying.

As many layers may be deposited on the substrate as is desired. Typically, a plurality of layers is applied. Each layer deposited on to the substrate is typically less than about 10 microns in thickness. With multiple depositions, a thick layer of coating can be built up. It should be noted that the composition of each sequential layer of the multiple deposition may be of different perfluoropolymer mixtures, if desired.

In step (iv), the solvent is at least partially removed from the one or more deposited layers by applying an amount of energy to the substrate or one or more deposited layers to raise the temperature of the one or more deposited layers to a temperature that is sufficient to evaporate the one or more perfluorosolvents in step (i) to at least partially de-solvate the one or more deposited layers. The energy is typically applied using directional heating. This means that the heating is hotter on one side than another, in order to prevent or minimise the formation of bubbles on the surface of the perfluoropolymer material, as well as to prevent or minimise the formation of any other undesirable imperfections. While it will be appreciated that in order to remove a solvent from the substrate or one or more deposited layers it is not required to apply sufficient energy to raise the temperature thereof to a temperature that is greater than the highest boiling point of the one or more perfluorosolvents in step (i) and that temperatures below this level will also effectively remove the solvent, typically, the temperature of the substrate or one or more deposited layers is raised to a temperature that is greater than the highest boiling point of the one or more perfluorosolvents in step (i). Further, if desired, the heating step (iv) may be repeated as many times as necessary.

When the perfluoroelastomeric material is being cured, there are three established mechanisms for the cross-linking of the perfluoropolymer that are used in the curing process of these materials:

Diamine crosslinking using a blocked diamine. In the presence of basic media, a monomer such as vinylidene fluoride is vulnerable to dehydrofluorination which enables the addition of the diamine to the polymer chain. Typically, magnesium oxide is used to catch the resulting hydrofluoric acid, forming magnesium fluoride and water. Diamine curing provides superior rubber-to-metal bonding properties as compared with other crosslinking mechanisms.

Ionic crosslinking (dihydroxy crosslinking), which provides superior heat resistance, improved hydrolytic stability and better compression set than diamine curing. In contrast to diamine curing, the ionic mechanism is not an addition mechanism but an aromatic nucleophilic substitution mechanism. Dihydroxy aromatic compounds are used as the crosslinking agent and quaternary phosphonium salts are typically used to accelerate the curing process.

Peroxide crosslinking, which proceeds via a free radical mechanism. Peroxide crosslinking is often the system of choice in aqueous and nonaqueous electrolytes.

Typically, the substrate is heated while the mixture from steps (i) and (ii) is deposited thereon. When multiple layers are deposited on the substrate, each layer is desirably substantially free of perfluorosolvent before the next layer is deposited. Preferably, evaporation at room temperature is used in order to avoid use of heat. Once a semi-solid matrix is formed by such solvent removal step, and the matrix is cured, the porogen may be removed from the solid matrix. This step may be accomplished by using a liquid or gaseous vehicle which is inert to the perfluoropolymer in the perfluoropolymer material, but capable of reacting with, dissolving and/or ionically bonding with the porogen in order to remove it from the matrix. Most preferred, the porogen is removed from the solid matrix by washing with water or a dilute acid such as a Bronsted acid, including hydrochloric, nitric or sulfuric acid or a conventional alcohol. The solid cured matrix, which is fairly stiff becomes less stiff, and much more pliable, flexible and elastomeric in nature after removal of the porogen. Typically, the perfluoropolymer material may be cured using the preferred temperature or other curing conditions for the specific perfluoropolymer material and curing system. Curing may include optional post curing steps for such compositions if desired. After curing and subsequent removal of the porogen, a cellular perfluoropolymer is thus formed having a plurality of open cells.

The material may be shaped, transfer molded, compression molded, extruded or the like, cured and then treated to extract the porogen. Various extraction techniques may be used, provided that the porogen is substantially removed and more preferably completely removed. It will be understood that the order and particular steps for shaping the material, curing, molding and/or extracting may be varied so long as the perfluoropolymer material is cured and the porogen extracted from the perfluoropolymer material.

The perfluoropolymer material has a sound structural integrity even before the curing step (v) is carried out.

The curing temperature of the perfluoropolymer material will vary depending upon the type of composition used as well as the curing system. One of ordinary skill in the art will understand that curing conditions vary with different elastomer systems, though such perfluoropolymer materials start to cure at temperatures above about 280° F. (138° C.). While a higher temperature can provide for a more rapid cure time, care must be taken not to use a curing temperature that is excessively high and which might cause any thermal degradation of the substrate.

The heat that is applied may be applied using a variety of heat sources, such as heat produced from an exothermic reaction or other heat exchange system, heated molds, a curing oven, radiative energy and the like. Preferably, the term "heating" as used herein includes any application of heat, radiative energy or any other form of energy capable of removing the solvent, ideally at a rapid rate, and/or curing the perfluoropolymer material. However, typically the substrate is heated using either inductive heating, convective heating, using a hot zone to induce evaporation of solvent from the deposited layer, or conductive heating, wherein the substrate is heated in a conductive manner to create a hotter region thereon; or via radiative heating, or via a combination of any two or more of these heating methods. Inductive heating is desirable as it is non-contact and is more preferable when making medical devices.

According to a further aspect of the invention, there is provided a perfluoroelastomeric product that is made according to the method as defined hereinabove.

According to a further aspect of the invention, there is provided a use of the perfluoroelastomeric product that is made according to the method as defined hereinabove in a medical device, such as for implants, grafts, insertable medical devices, cardiovascular prostheses, grafts, tissue engineered products utilizing synthetic lattices (which act as a scaffold for the growth of human or animal cells within the scaffold), sutures, in sealing members, in fuel cell membranes, or coatings on orthopaedic implants.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the scope of the present invention as defined by the appended claims.

The invention claimed is:

1. A process for the processing of a perfluoropolymer material, the process comprising the steps of:
   i) Dissolving one or more uncured perfluoropolymer materials in a solvent containing one or more liquid perfluorinated solvent(s) to form a solution;
   ii) Applying the resultant solution formed in step (i) to a substrate to apply multiple depositions on the substrate, wherein an amount of energy is applied directly only to the substrate to raise the temperature of the multiple depositions to a temperature sufficient to at least partially remove the solvent from the multiple depositions while the resultant solution formed in step (i) is applied in multiple depositions, wherein the substrate comprises a metallic mandrel, a non-metallic mandrel, a metallic implant, or a non-metallic implant; and
   (iii) Curing the perfluoropolymer materials within the multiple depositions to form a perfluoroelastomeric product.

2. A process according to claim 1, wherein the one or more perfluoropolymer materials comprise one or more selected from tetrafluoroethylene (TFE), hexafluoropropylene (HFP), and perfluoroalkylvinyl ethers (PAVEs), or a perfluoroalkoxyvinyl ether.

3. A process according to claim 2, wherein the perfluoroalkylvinyl ethers contain alkyl groups that are either straight or branched, and which include one or more ether linkages selected from perfluoro (methyl vinyl ether), perfluoro (ethyl vinyl ether), perfluoro (propyl vinyl ether).

4. A process according to claim 1, wherein the perfluoroelastomeric product comprises a crosslinked terpolymer of tetrafluoroethylene, a perfluoroalkylvinyl ether, and at least one perfluorinated curesite monomer which incorporates a functional group to permit crosslinking of the terpolymer.

5. A process according to claim 4, wherein the curesite monomer comprises a cyano, a bromo, iodo or pentafluorophenoxy functional group.

6. A process according to claim 1, wherein the resultant solution from step (i) is applied to the substrate in step (ii) using a method selected from:
   Pneumatic spraying
   Electrostatically focused pneumatic spraying
   Electrospraying
   Ultrasonic spraying
   Syringing
   Electrostatic spinning
   Inkjet printing
   Brushing/painting.

7. A process according to claim 1, wherein in step (i) only one solvent is used.

8. A process according to claim 1, wherein the solvent is completely removed.

9. A process according to claim 1, wherein the step (iii) of curing the perfluoropolymer materials is carried out when the perfluoropolymer materials are on the substrate.

10. A process according to claim 1, wherein the step (iii) of curing the perfluoropolymer materials is carried out when the perfluoropolymer materials are not on the substrate.

11. A process according to claim 1, further comprising adding one or more porogens and/or one or more functional additives to the solution formed in step (i).

12. A process according to claim 11, further comprising a step of removing the porogen from the perfluoroelastomeric product after step (iii).

13. A process according to claim 11, wherein the one or more porogens comprise one or more materials selected from sodium chloride, salicylic acid, lactose, valine, sodium bicarbonate, sodium hydrogen carbonate, calcium carbonate, glycine, polyethylene oxide, polyethylene glycol (PEG), polyvinylpyrrolidone, polyvinyl chloride, and/or titanium dioxide.

14. A process according to claim 1, further comprising a step (iv) of forming a product consisting of the perfluoroelastomeric product.

15. A process according to claim 1, further comprising a step of adding one or more porogens to the solution formed in step (i) to form a mixture.

16. A process according to claim 1, further comprising a step of adding one or more functional additives to the solution formed in step (i) to form a mixture.

17. A process according to claim 16, wherein the functional additive comprises one or more selected from co-agents, processing aids, fillers, acid acceptors, cure accelerators, glass fibers, polyaramid fibers, curatives and/or plasticizers.

* * * * *